United States Patent [19]

Kato et al.

[11] Patent Number: 4,656,260
[45] Date of Patent: Apr. 7, 1987

[54] CYCLIC PYRAZOLO C-NUCLEOSIDE COMPOUND AND PROCESS FOR PREPARING THE SAME

[75] Inventors: Tetsuzo Kato; Nobuya Katagiri, both of Sendai, Japan

[73] Assignee: Kanto Ishi Pharmaceutical Co., Ltd., Tokyo, Japan

[21] Appl. No.: 686,998

[22] Filed: Dec. 27, 1984

[51] Int. Cl.$^4$ ............................................... C07H 7/06
[52] U.S. Cl. ..................................... 536/55; 536/1.1; 536/55.3; 536/18.7
[58] Field of Search ..................... 536/1.1, 53, 55, 55.3

[56] References Cited

U.S. PATENT DOCUMENTS 3,998,999 12/1976 DeBernardo et al. ................ 536/55

OTHER PUBLICATIONS

Nobuya Karagiri et al., J. Chem. Soc. Perkin Trans. I, "Synthesis of Pyrazofurin and Its Analogues", pp. 553–560, 1984.
Just et al., "Can. Jour. Chem.", vol. 54, No. 18, 9/15/76, pp. 2935–2939.

Primary Examiner—Johnnie R. Brown
Attorney, Agent, or Firm—Oblon, Fisher, Spivak, McClelland & Maier

[57] ABSTRACT

A novel compound, 3-($\beta$-D-ribofranosyl)pyrazolo-[3,4-e][1,3]oxazine-5,7-dione, exhibiting a function of inhibiting propagation or growth of various virus, and a process for preparing the same.

7 Claims, No Drawings

CYCLIC PYRAZOLO C-NUCLEOSIDE COMPOUND AND PROCESS FOR PREPARING THE SAME

BACKGROUND OF THE INVENTION

1. Field of the Invention

The present invention relates to a novel cyclic pyrazolo compound, 3-(β-D-ribofranosyl)pyrazolo[3,4-e][1,3]oxazine-5,7-dione (hereinafter briefly referred to as pyrazolo[3,4-e]oxazine C-nucleoside), represented by the following formula:

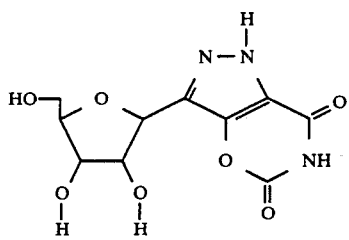

and a process for preparing the same.

2. Discussion of the Background

Pyrazofurine (pyrazomicine) is a C-nucleoside isolated from a liquid culture medium of Streptomyces candidus and represented by the following formula:

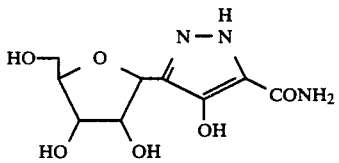

The pharmaceutical properties of the aforementioned pyrazomicine have attracted general attention in recent years. Further details of the compound and the pharmaceutical properties thereof will be found, for example, in G. D. Daves Jr., et al, Prog. Med. Chem. 13, 303(1976); and K. Gerzon et al, the Second International Congress of Heterocyclic Chemistry (ICHC), Collection of Summary of Reports, page 131(1969). These articles will be incorporated herein as references.

However, only three synthetic processes, other than the biochemical culture method, have been reported up to now. These three preceding synthetic processes are disclosed in J. Farkas et al, Tetrahedron Letters, 1972, 2279; S. De Bernardo et al, J. Org. Chem., 41, 287 (1976); and J. G. Buchanan et al, J. Chem., Soc. Perkin I. 2374 (1981).

However, these known processes have defects in connection with yield, selection of starting materials and reaction sequence, making it desirable to provide an improved process.

In view of the aforementioned circumstances, we have already proposed a simplified process for preparing pyrazomicine from 3-alkoxylcarbonyl-2-oxo-propylidene triphenyl-phosphorane represented by the general formula ph$_3$PCH.COCH$_2$CO$_2$R. The reaction sequence of our earlier proposed process will be shown below by the reaction formulae, and the details thereof can be found in, for example, Japanese Laid-Open Patent Publication No. 134088/1983, the disclosure of which is incorporated herein as a reference.

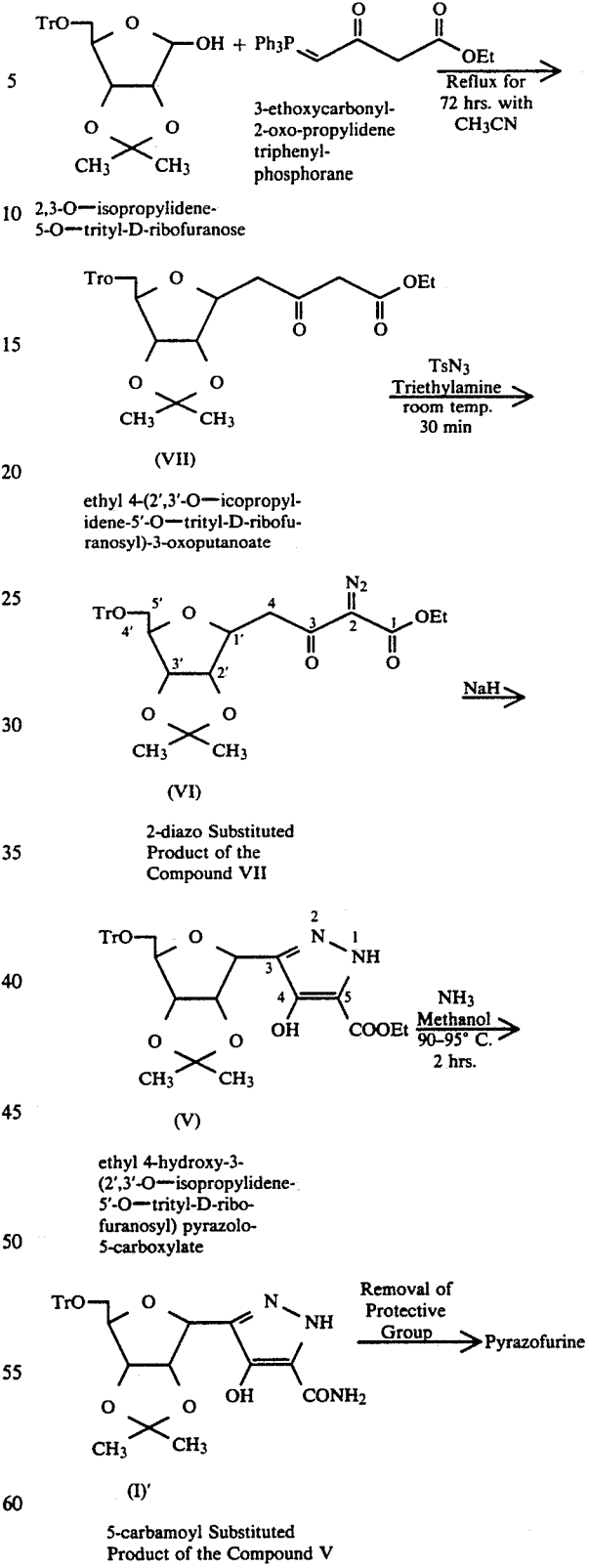

SUMMARY OF THE INVENTION

A primary object of this invention is to provide a novel derivative of pyrazofurine. Pyrazofurine is a compound which has attracted attention as having an antitumor efficacy (reference should be made to M. J. Sweeny et al, Cancer Res., 33, 2619 (1973)) and as having an antibiotic function (G. E. Gutowski et al, Ann. N. Y. Acad Sci., 255, 544 (1975).

Another object of this invention is to provide a convenient process for preparing the derivative of pyrazofurine described above.

Accordingly, one aspect of the present invention is directed to a novel pyrazolo[3,4-e]oxazine C-nucleoside which can be effectively used for the inhibition of various virus and is represented by the following formula:

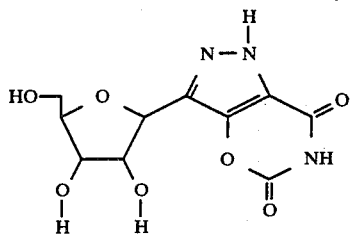

(III)

According to a further aspect of the invention, there is provided a process for preparing 3-(β-D-ribofranosyl)pyrazolo[3,4-e][1,3]oxazine-5,7-dione comprising the steps of: reacting 3-(2',3',5'-o-substituted-β-D-ribofranosyl)-4-hydroxy-5-carbamolypyrazole represented by the following formula:

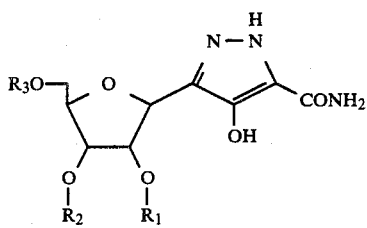

(I)

wherein $R_1$ and $R_2$ are, respectively, aralkyl, aroyl, trityl, or benzyl, or $R_1$ and $R_2$ are combined together to form an isopropylidene group including the bond carbon atom, and $R_3$ is aralkyl, aroyl, trityl or benzyl; with a carbonylation agent (IV) in a nonpolar solvent and in the presence of a metal hydride to produce 3-β-D-ribofranosyl-1H,3H-pyrazolo[3,4-e][1,3]oxazine-5,7-dione represented by the following formula:

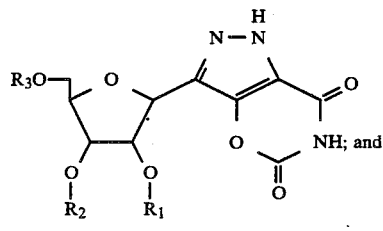

(II)

removing the protection groups $R_1$, $R_2$ and $R_3$.

The process of this invention has been developed through energetic research work toward improvement of the process disclosed in our previous patent application (Japanese Laid-Open Patent Publication No. 134088/1983). The process of this invention can be represented by the sequential reactions set forth hereinbelow.

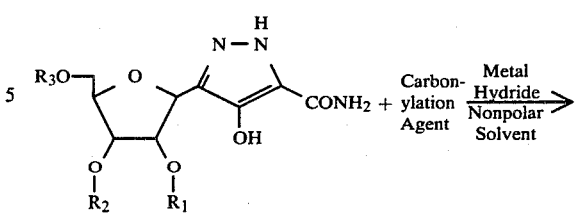

(I)

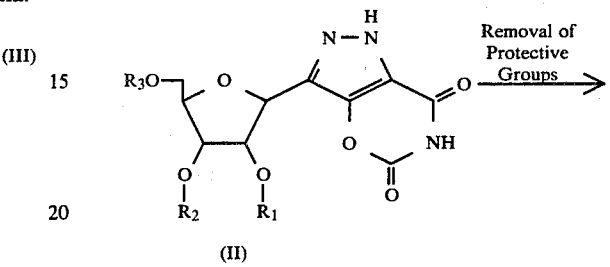

(II)

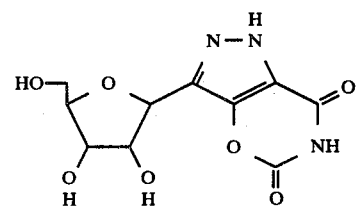

(III)

DETAILED DESCRIPTION OF THE PREFERRED EMBODIMENTS

The process of the present invention will now be described in detail.

(A) Starting Material (I):

The starting material (I) may be readily prepared following the known method, as disclosed in the specification of our previous patent application. An example of a process for the preparation of the starting material (I) will be described more specifically, as follows.

The known 3-alkoxylcarbonyl-2-oxopropylidene triphenyl-phosphorane, ph$_3$PCH.COCH$_2$CO$_2$R, (F. Serratosa et al., An: R. Soc. Esp. Fis. Quim., 62, 431 (1966)) is heated with a protected ribofuranose, such as 2,3-o-isopropylidene-5-o-trityl-o-ribofuranose, in an inert solvent for a long time (50 to 90 hrs) to produce 4-C-(2',3'-o-isopropylidene-5'-o-trityl-D-ribofranosyl)acetoacetate (VII) which is a C-glucoside of acetoacetoacetic ester. Solvents usable as the inert solvent in the aforementioned step include benzene, toluene and nitromethane, and acetonitirle is particularly preferred. The reaction proceeds substantially quantitatively. The reaction product is then subjected to diazotization using tosylazide. The diazotization reaction may be carried out in an inert solvent, such as acetonitrile, by allowing the reaction mixture to stand at ambient temperature to form a diazo derivative (VI) at a high yield (94%).

The diazo derivative (VI) is dissolved in an inert solvent, e.g. dimethyleneglycol dimethyl ether, and stirred at room temperature for a few hours in the presence of an alkali metal hydride, such as sodium hydride, to effect ring closure or cyclization, whereby a pyrazole derivative, 3-(2',3'-o-isopropylidene-5-trityl-D- ribofuranosyl)-4-hydroxy-pyrazole-5-carboxylate (V), is formed. This cyclization reaction may be carried out in an inert gas atmosphere, such as nitrogen gas stream, to attain a high yield (82%).

The thus formed ester (V) is then subjected to conventional ammonolysis, for example, by heating in a sealed tube with an ammonia-methanol solution at 90° to 95° C. to obtain the desired amide, 3-(2',3'-o-isopropylidene-5'-trityl-D-ribofuranosyl)-4-hydroxy-pyrazole-5-carboxamide (I'). The reaction is completed within 2 hours at high yield (94%).

(B) Carbonylation Agent:

Conventional carbonylation agents may be used as the carbonylation agent in the process of the invention, examples being carbonic acid derivatives, such as diethyl carbonate, and 1',1'-carbonyl-di(s)tiazine, and particularly good results can be obtained by the use of 1,1'-carbonyl di-imidazole.

(C) Metal hydride forming agent:

Materials usable for this purpose include alkali metals, such as lithium, potassium and sodium, hydrides of alkali metal, and metallization agents, such as phenyl lithium in the presence of a secondary amine. Particularly preferred is sodium hydride.

(D) Nonpolar Solvent:

A variety of known nonpolar solvents, including hydrocarbons and ethers, may be used, examples being diethyl ether, 1,2-dimethoxyethane, diethyleneglycol dimethyl ether, tetrahydrofuran, dioxane, hexane and toluene. Other nonpolar solvents may be conveniently used provided that they are inert with respect to the starting material and can dissolve the starting material completely.

(E) Condition for Cyclization Reaction:

The starting material amide (I) is deprived of an active hydrogen, or added with an active hydrogen, by the use of a metallization agent, such as NaH, added in an amount of 0.5 molar equivalent per unit molar equivalent of the amide contained in a nonpolar solvent cooled by an ice bath. Then, 2 molar equivalents of 1,1'-carbonyl di-imidazole per a 1 molar equivalent of the amide (I) are added, followed by agitation at normal temperature (20° to 25° C.) for about 10 hours. The reaction is carried in an inert gas atmosphere, for example, under passage of an argon or nitrogen stream.

(F) Removal of Protective Groups:

The protective groups may be removed or eliminated through the conventional processes.

When trityl or isopropylidene groups are used as the protective groups, they may be readily removed by the use of trifluoroacetic acid at room temperature. The reaction is completed within an hour. On the other hand, when benzyl groups are used as the protective groups, removal thereof may be effected with boron trichloride in methylene dichloride. The latter-mentioned process is carried out at a low temperature in the vicinity of $-78°$ C. for about 4 hours. After the completion of the protective group removal reaction, the solvent is distilled off at a low temperature of not higher than about 5° C. under reduced pressure, and the residue is refined through column chromatography.

As should be appreciated from the foregoing description, the starting material used in the process of the present invention is easily available, and the process has an additional advantage that the objective compound can be prepared at high yield through simplified process steps.

Moreover, the product, 3-($\beta$-D-ribofranosyl)-pyrazolo[3,4-e][1,3]oxazine-5,7-dione, is a novel compound which has a function of inhibiting growth or propagation of various virus. It has also been ascertained that the toxicity of the compound is of substantially the same level as that of pyrazofurine.

DESCRIPTION OF THE PREFERRED EMBODIMENTS

The present invention will be described more specifically by referring to Examples thereof.

EXAMPLE 1

Preparation of 3-($\beta$-D-ribofranosyl)pyrazolo[3,4-e][1,3]oxazine-5,7-dione(III)

To 15 ml of an anhydrous dimethoxyethane suspension containing 72 mg of 50% sodium hydride dispersion in oil cooled on an ice bath and purged with a nitrogen stream, there was added dropwise 20 ml of an anhydrous dimethoxyethane solution containing 1.76 g of 3-(2',3'-o-isopropylidene-5'-o-trityl-$\beta$-D-ribofranosyl)-4-hydroxy-5-carbamoylpyrazole (represented by the formula I wherein $R_1+R_2$ is isopropylidene and $R_3$ is trityl). After addition of 5 ml of an anhydrous dimethoxyethane solution containing 0.97 g of 1,1'-carbonyldiimidazole, the reaction mixture was agitated at room temperature for 10 hours. After the completion of reaction, 1 ml of a dimethoxyethane solution containing 90 mg of acetic acid was added, followed by agitation and concentration under reduced pressure. The residue was dissolved in ether, and then the ether phase was washed with water, dried, concentrated and treated through silica-gel column chromatography. From the eluate of the column chromatography carried out using n-hexane/ethyl acetate (2:1) as a developer, a colorless sticky paste-like substance, 3-(2',3'-o-isopropylidene-5'-o-trityl-$\beta$-D-ribofranosyl)pyrazolo[3,4-e][1,3]oxazine-5,7-dione (represented by the formula II wherein $R_1+R_2$ is isopropylidene and $R_3$ is trytyl) was obtained. Yield: 1.1 g (56%).

Infrared Absorption Spectrum (CHCl$_3$): 3400, 1775, 1740 cm$^{-1}$; Ultimate Analysis ($C_{32}H_{29}N_3O_7$·AcOEt)

Calcd.: C, 65.94; H, 5.69; N, 6.41; Found: C, 65.72; H, 5.66; N, 6.40.

0.3 gram of the product set forth above was dissolved in trifluoroacetic acid (3 ml), allowed to stand at the room temperature (20° C.) for an hour, and then concentrated under reduced pressure. The residue was subjected to silica-gel column chromatography. From the eluate of the column chromatography carried out using ethyl acetate/acetone/methanol/water (47:1:1:1) as a developer, a colorless sticky paste-like substance [(C-nucleoside (III)] was obtained. Yield: 0.15 g (Quantitative Yield).

Infrared Absorption Spectrum (KBr): 3600–2800, 1770(s), 1720 cm$^{-1}$

Ultimate Analysis ($C_{10}H_{11}N_3O_7$·0.7CH$_3$COCH$_3$)

Calcd.: C, 41.78; H, 4.52; N, 13.65; Found: C, 42.16; H, 4.34; N, 13.32.

EXAMPLE 2

0.12 g of a 20% sodium hydride purum powder in white oil was suspended in 20 ml of anhydrous diethyleneglycol dimethyl ether, cooled on an ice bath and purged with a nitrogen stream. The suspension was added with 20 ml of an anhydrous diethyleneglycol dimethyl ether solution containing 1.2 g of an amide (represented by the general formula I wherein $R_1+R_2$ is isopropylidene and $R_3$ is trityl) dropwisely. A solution of 1,1'-carbonyl di-imidazole (0.65 g) in anhydrous diethyleneglycol dimethyl ether (5 ml) was added dropwisely, and then the reaction mixture was agitated at room temperature for 12 hours.

After the completion of reaction, 60 mg of acetic acid was added to the mixture, followed by additional agitation, and then concentration under reduced pressure to obtain a residue which was dissolved in ether, washed with water, dried and concentrated. The concentrated residue was treated through silica-gel column chromatography using n-hexane/ethyl acetate (2:1) as a developer to obtain an eluate from which a cyclic product of pyrazolooxazine (represented by the general formula II wherein $R_1+R_2$ is isopropylidene and $R_3$ is trityl) was obtained. Yield: 0.6 g (46%). The product was identified through IR and NMR analyses.

0.5 g of the aforementioned product was dissolved in 5 ml of trifluoroacetic acid. After the solution had been allowed to stand at the room temperature for an hour, it was concentrated under reduced pressure and then treated through silica-gel column chromatography to obtain the object substance I in the form of colorless foam. Yield: 0.25 g (Quantitative Yield). The product was identified as the same compound as obtained previously in Example 1 by comparing the results of IR and NMR analyses.

The pyrazolo[3,4-e]oxazine C-nucleoside (the compound (III)) obtained through the process described in detail in the Examples was examined for its poisonous action on organic cells and its antivirus activities by culturing experiments using Hela cell, Vero B cell, Vero Flow cell and Kidney cell of Old World rabbit (Oryctolagus cuniculus). The compound was found to be substantially equivalent to pyrazofurine in poisonous action on organic cells and to have antivirus activities on a variety of virus substantially equivalent to or even superior over those of pyrazofurine.

What is claimed is:

1. 3-($\beta$-D-ribofranosyl)pyrazolo[3,4-e][1,3]oxazine-5,7-dione.

2. A process for the preparation of 3-($\beta$-D-ribofranosyl)-pyrazolo[3,4-e][1,3]oxazine-5,7-dione, comprising:

(i) reacting 3-(2',3',5'-o-substituted-$\beta$-D-ribofranosyl)-4-hydroxy-5-carbamoylpyrazole of the formula:

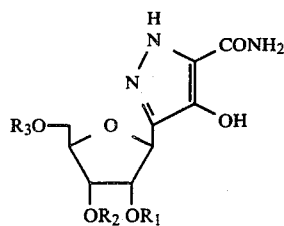

wherein $R_1$ and $R_2$ are each independently an aralkyl group or an aroyl group or $R_1$ and $R_2$ are combined together to form an isopropylidene group, and $R_3$ is an aralkyl group or an aroyl group, with a carbonylation agent in a non-polar solvent in the presence of a metal hydride to produce 3-$\beta$-D-ribofranosyl-1H,3H-pyrazolo[3,4-e][1,3]oxazine-5,7-dione of the formula:

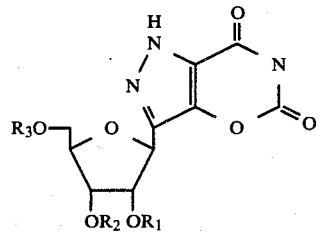

and:

(ii) removing the groups $R_1$, $R_2$ and $R_3$.

3. The process according to claim 2, wherein the said nonpolar solvent is at least one member selected from the group consisting of diethyl ether, dimethoxyethane, diethyleneglycol dimethyl ether, tetrahydrofuran, dioxane, hexane, toluene and mixtures thereof.

4. The process according to claim 2, wherein the said metal hydride is sodium hydride.

5. The process according to claim 2, wherein the said carbonylation agent is 1,1'-carbonyl-dimidazole.

6. The process of claim 2, wherein $R_1$ and $R_2$ are each independently a trityl group or a benzyl group.

7. The process of claim 2, wherein $R_3$ is a trityl group or a benzyl group.

* * * * *